United States Patent [19]

Both

[11] Patent Number: 6,020,172
[45] Date of Patent: Feb. 1, 2000

[54] NUCLEIC ACID DELIVERY WITH OVINE ADENOVIRAL VECTORS

[75] Inventor: Gerald Wayne Both, North Ryde, Australia

[73] Assignee: Commonwealth Scientific and Industrial Research Organisation, Campbell, Australia

[21] Appl. No.: 09/011,525

[22] PCT Filed: Aug. 14, 1996

[86] PCT No.: PCT/AU96/00518

§ 371 Date: Apr. 20, 1998

§ 102(e) Date: Apr. 20, 1998

[87] PCT Pub. No.: WO97/06826

PCT Pub. Date: Feb. 27, 1997

[30] Foreign Application Priority Data

Aug. 14, 1995 [AU] Australia ............................... PN 4776

[51] Int. Cl.[7] ........................... C12N 15/64; C12N 15/86; C12N 5/10
[52] U.S. Cl. ..................................... 435/91.41; 435/320.1; 435/235.1; 435/455; 435/456; 435/366; 435/371; 435/372
[58] Field of Search .............................. 435/320.1, 172.1, 435/172.3, 69.1, 455, 456, 366, 235.1, 371, 372, 91.41, 91.4; 424/93.2, 93.6

[56] References Cited

FOREIGN PATENT DOCUMENTS

| 67878/94 | 12/1994 | Australia . |
| 72646/94 | 2/1995 | Australia . |
| 11891/95 | 6/1995 | Australia . |
| 29731/95 | 2/1996 | Australia . |
| 35250/95 | 4/1996 | Australia . |
| 36584/95 | 5/1996 | Australia . |
| 38477/95 | 5/1996 | Australia . |
| WO 95/07718 | 3/1995 | WIPO . |
| WO 96/03508 | 2/1996 | WIPO . |

OTHER PUBLICATIONS

Chen et al., PNAS, vol. 94, pp. 1645–1650, Mar. 1997.
Verma et al., Nature, vol. 389, pp. 239–242, Sep. 18. 1997.
Orkin et al., "Report and Recommendations of the Panel to Assess the NIH Investment in Research on Gene Therapy", Dec. 7, 1995.

Vrati et al., "Sequence of Ovine Adenovirus Homologs for 100K Hexon Assembly, 33K, pVIII, and Fibre Genes: Early Region E3 is Not in the Expected Location", Virology, vol. 209, Jun. 1, 1995, pp. 400–408.

Vrati et al., "Construction and Transfection of Ovine, adenovirus Genomic Clones to Rescue Modified Viruses", pp. 200–203.

Vrati et al., "Unique Genome Arrangements of an Ovine Adenovirus: Identification of New Proteins and Proteinase Cleavage Sites", (1996), pp. 86–199.

Lemarchand et al., "In Vivo Gene Transfer and Expression in Normal Uninjured Blood Vessels using replication–Deficient Recombinant Adenovirus", pp. 1132–1138.

Boyle David B. et al., "Characterisation of Australian ovine adenovirus isolates", Veterinary Microbiology, vol. 41, No. 3, 1994, pp. 281–291.

Stevenson, Susan C. et al, "Human Adenovirus Serotypes 3 and 5 Bind to Two Different Cellular Receptors via the Fiber Head Domain", Journal of Virology, May 1995, vol. 69, No. 5, pp. 2850–2857.

Taneja, Samir S. et al., "In vitro target specific gene therapy for prostate cancer utilizing a prostate specific antigen promoter–driven adenoviral vector", Proceedings of the American Association for Cancer Research, vol. 35, Mar. 1994, pp. 375, abstract #2236.

*Primary Examiner*—David Guzo
*Attorney, Agent, or Firm*—McDermott, Will & Emery

[57] ABSTRACT

A method of delivering a nucleic acid molecule to a human cell which involves exposing to the cell a viral vector containing a DNA molecule including a nucleic acid sequence encoding the genome of an ovine adenovirus capable of infecting human cells or functionally equivalent nucleic acid sequence or portion thereof and at least one nucleic acid sequence encoding a gene to be expressed in the cell, such that the vector infects the cell and the infected cell expresses the gene.

51 Claims, 8 Drawing Sheets

INFECTION WITH OAV206 (HCMV/VP7sc)
48HR P.I.

INFECTION WITH OAV206 (HCMV/VP7sc)
48 HR p.i.

INFECTION WITH OAV206 (HCMV/VP7sc) 36hr p.i.

INFECTION WITH OAV204 (MLP/VP7sc)
36hr p.i.

OAV FIBER STALK REPEATING UNITS

24.     N A L M V P K L G T G L S F D S (SEQ ID NO:1)
25.     T G A I T V G N K N N D K L (SEQ ID NO:2)     422

START HEAD REGION

TLWTTPAPSPNCRLNAEKDAKLTLVLTKCGSQILATVSVLAVKGSLAPISGTVQS
AHLIIRFDENGVLLNNSFLDPEYWNFRNGDLTEGTAYTNAVGFMPNLSAYPKSH
GKTAKSNIVSQVYLNGDKTKPVTLTTTLNGTQETGDTTPSAYSMSFSWDWSGH
NYINEIFATSSYTFSYIAQQ (SEQ ID NO:3)

FIG.3

236     LTKGNISPLL*LDVDAYQASLK*(SEQ ID NO:4)...42aas......*RGD*...29aas...*KPQKKP*
        *VLEPVMQDEN* GVSYNEKIS (SEQ ID NO:5)

FIG.4

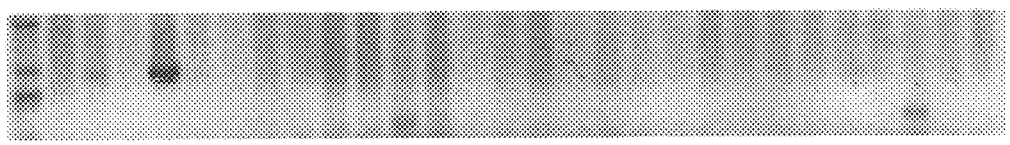
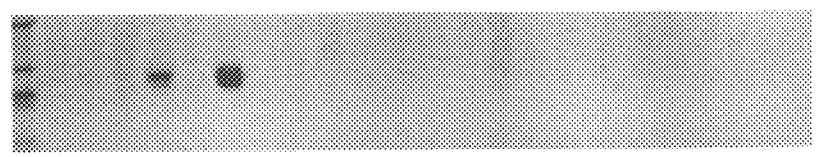
FIG.7

NUCLEIC ACID DELIVERY WITH OVINE ADENOVIRAL VECTORS

TECHNICAL FIELD

The present invention relates to methods for gene therapy in humans using novel ovine adenoviral vectors. In particular, the present invention is directed to methods of introducing genes into human cells such that the genes are functionally expressed by the cells.

BACKGROUND ART

Genetic defects which cause diseases such as cancer, cystic fibrosis, muscular dystrophy and many other disorders contribute greatly to the cost of human health care. Consequently, there are major research efforts worldwide to develop new approaches to provide genetic therapy effective at the level of the somatic cell.

Central to this work are a variety of gene vectors derived from viruses such as retro-, pox, adeno-associated and adenoviruses. The viruses from which these vectors are derived are of low pathogenicity and the vectors are designed to carry therapeutic genes into the host cell. Under appropriate conditions these may produce products which can vaccinate the host, change cell phenotypes, stimulate immune responses, supplement genetic defects or lead to cell death.

No single viral vector has all the attributes desirable for all therapeutic situations. Some vectors are better suited to particular tasks than others because of their biological properties. For example, as retroviruses can integrate into the host genome, these vectors appear to be well suited to deliver genes to dividing cells such as the stem cells of the haemopoietic cell lineage. In contrast, adenovirus vectors do not usually integrate their DNA but are able to efficiently infect non-dividing cells. Human adenoviral vectors have been used to deliver genes to a variety of tissues in humans and in animal models, eg, lungs, muscle, liver, vascular and brain cells. A major disadvantage of the use of human adenoviruses is that as these viruses naturally infect humans, it can often be the case that the person to be treated with the human adenoviral vector has circulating antibodies which can neutralise the vector prior to it reaching the target cell. Immunity also results in efficient clearance of the virus from the host by the cellular immune system, thereby rapidly diminishing any therapeutic effect due to gene expression. Thus, there is a need to develop vectors derived from viruses that normally do not infect humans, so as to overcome the problem of pre-existing immunity. As ovine and human adenoviruses are serologically distinct, the use of an ovine adenovirus (OAV) as a vector may achieve this objective. It is also essential to develop vectors whose presence in the host is disguised so that the immune response is less severe and gene expression is more likely to persist. As ovine adenovirus does not replicate productively, even in most non-ovine animal cells (1) it was expected to replicate abortively in human cells, provided that it could infect them. A block in replication at all early step would lead to minimal expression of viral products in the infected cell, with a consequent low level induction of the cellular immune response.

The present inventors have developed an adenoviral vector derived from ovine adenovirus OAV287. The virus and viral vectors derived therefrom are fully described in International Patent Application Number WO 96/03508 filed on Jul. 26, 1995 in the name of Commonwealth Scientific and Industrial Research Organisation (hereinafter referred to as "the PCT Application" and incorporated herein by reference). The adenoviral vector disclosed in the PCT Application was found to be suitable for use as a vector to introduce foreign DNA into a variety of non-human cells, and in particular into sheep cells. The genome sequence and arrangement of OAV287 is different from all known human, animal and avian adenoviruses, including the canine adenovirus described in International Patent Application Numbers WO 91/11525 and WO 94/26914, the bovine adenovirus described in International Patent Application Number WO 95/16048 and the avian CELO isolate (2). OAV is also serotypically distinct (1) and is not neutralised by serum human Ad5. This is consistent with the distinctive amino acid sequences in the hexon, penton and fiber antigens (3). There are also other major differences in the capsid proteins of OAV compared with other known adenoviruses. OAV lacks capsid protein homologues V and IX but contains at least two other structural proteins (3). Due to the low nucleotide sequence homology between OAV and other adenoviruses there is little chance of recombination between OAV and another adenovirus during co-infection in the host to form an infectious recombinant virus.

Critical to the use of OAV vectors for human gene therapy is the question of whether OAV call actually enter human cells. Entry of human adenoviruses into human cells occurs via a two step process involving specific amino acid sequences in the fiber and penton base proteins (4, 5). First the virus attaches to an unidentified surface receptor via the trimeric fiber protein which protrudes from the surface of the virus. Secondly, an interaction occurs (primarily) between the $\alpha_v \beta_v$ class of integrins and an Arg/Gly/Asp (RGD) tri-peptide which forms part of the penton protein complex at the base of the fiber spike (6). The virus is then taken into the cell by endocytosis. The cell binding domain of the ovine adenovirus OAV287 fiber protein is smaller and has a completely different sequence to its human adenovirus homologues. It almost certainly binds to a different primary receptor. Compared with human adenoviruses, the OAV penton protein also lacks the critical RGD motif and flanking sequences (3). Thus, it was not known, nor could it be predicted. whether OAV including OAV287 would infect human cells.

The present inventors have made the surprising discovery that, despite the major differences in its cell attachment proteins, viral vectors derived from ovine adenovirus OAV287 can infect a variety of, but not all, human cell lines. This finding paves the way for the use of OAV as a human gene therapy vector.

DISCLOSURE OF INVENTION

In a first aspect, the present invention consists in a method of gene therapy in a human subject comprising administering to the subject a viral vector comprising a DNA molecule including a nucleic acid sequence encoding the genome of ovine adenovirus or a functionally equivalent nucleic acid sequence or a portion thereof and at least one nucleic acid sequence comprising a gene to be expressed in the cell, such that the viral vector infects at least one cell of the subject and the infected cell expresses the gene.

In a preferred embodiment of the present invention, the genome of the ovine adenovirus is OAV287 or a nucleic acid molecule derived therefrom.

It is preferred that substantially no virus replication occurs in the cell. More preferably substantially no early or late viral gene expression occurs in the cell.

As used herein the term "functionally equivalent nucleotide sequence" is intended to cover minor variations in the ovine adenovirus sequence which, due to degeneracy in the DNA code, does not result in a virus having substantially different biological activities from the native ovine adenovirus. The encoded adenovirus proteins can have an altered amino acid sequences from the native virus sequences but should retain substantially the same biological activities as the native viral proteins. This may be achieved by various changes in the sequence, such as insertions, deletions and substitutions, either conservative or non-conservative, where such changes do not substantially alter the virus.

A gene is defined as any nucleic acid sequence that encodes a functional molecule. The gene may be an oncogene, a tumor suppressor gene, it may encode therapeutic molecules including antisense or ribozyme RNAs, a gene encoding an enzyme, a gene encoding a cytokine or other immune modulating macromolecule, a gene encoding a recombinant antibody, a gene encoding a lytic peptide, a gene encoding a vaccine antigen, a gene encoding a macromolecule which complements genetic defects in somatic cells, or a gene encoding a macromolecule which catalyses processes leading to cell death. Cell death may occur directly as a result of gene expression or indirectly as a result of an immune response to an expressed foreign macromolecule. Preferably the gene encodes an enzyme such as herpesvirus thymidine kinase or non-mammalian cytosine deaminase which metabolises a pro-drug and more preferably the gene encodes prokaryotic purine nucleoside phosphorylase. In the presence of the appropriate pro-drug, expression of the gene by the infected cell and metabolism of the pro-drug results in a toxic product which leads to cell death.

In a further preferred embodiment of the first aspect of the present invention, the viral vector includes a cell-specific promoter expressively linked to the gene, such that the gene is expressed only in a desired target cell. Such promoters are well known in the art. For example, for the treatment of prostate cancer a promoter could be selected from the group including, but not limited to promoters derived from the probasin, prostate specific antigen (PSA) or prostate specific membrane antigen (PSMA) genes. Similarly, for breast cancers, the erbB-2 promoter may be useful. For other cancers such as lung, the carcinoembryonic antigen (CEA) promoter could be used.

A more preferred embodiment of the first aspect of the present invention is the viral vector OAV211.

In a second aspect, the present invention consists in a method of gene therapy wherein the ovine adenoviral vector according to the first aspect of the present invention has one or more coding regions of the adenovirus genome modified. The modification preferably results in an altered coat protein of the virus. More preferably the altered coat protein is selected from the group consisting of fiber, hexon and penton base proteins.

The modification preferably involves the replacement of specific ovine adenoviral DNA regions with the equivalent coding regions from other animal or human adenoviruses.

A human adenovirus type 5/lacZ recombinant can infect CSL503 cells. It is therefore possible to substitute the cell binding domains from the Ad5 penton and fiber proteins for those regions in the OAV proteins while retaining the ability of the hybrid OAV to replicate in CSL503 cells. Such a hybrid virus will still replicate abortively in human cells. For example, exchanging the cell binding domain of the ovine adenovirus fiber protein for the equivalent domain from a human or animal adenovirus allows the hybrid OAV to infect a different spectrum of cells compared with the native OAV.

Similarly, a hybrid ovine adenovirus carrying the penton base RGD motif from a human adenovirus or the equivalent region from an animal adenovirus should be able to enter a wider variety of human and animal cells than wild-type OAV. A hybrid ovine adenovirus carrying both the fiber and penton protein modifications should efficiently bind and enter the same spectrum of cells as the adenovirus from which the cell-binding sequences were derived while retaining the abortive replication properties of the ovine adenovirus in non-ovine cells.

A more preferred embodiment of the second aspect of the present invention are the viral vectors OAV206/Ad5f and OAV206/Ad5p. In a further preferred embodiment is a viral vector which carries both modifications from OAV206/Ad5f and OAV206/Ad5p.

The viral vectors of the present invention can be administered at concentrations of $10^4$ to $10^{14}$, preferably $10^6$ to $10^{10}$, plaque forming units per ml topically, orally, or by injection. It will be appreciated that the amount administered and the route of administration will depend on the treatment or therapy desired.

In a third aspect, the present invention consists in a vaccine for use in the method of the first and second aspects of the present invention.

In order that the nature of the present invention may be more clearly understood, preferred forms will be described with reference to the following examples and drawings.

BRIEF DESCRIPTION OF DRAWINGS

FIG. 3 shows the amino acid sequence of the hybrid fiber protein in OAV206/Ad5f at the junction between the OAV sequences (underlined) and the Ad5 cell binding domain (SEQ ID NOS:1 to 3).

FIG. 4 shows the amino acid sequence of the modified penton protein in OAV206/Ad5p following the insertion of the Ad5 RGD motif, underlined residues signify the junctions between the OAV and Ad5 sequences (SEQ ID NOS:4 and 5).

FIG. 7 shows the analysis by RT-PCR of RNA transcripts for (A) penton (B) hexon and (C) GAPDH genes. RNA samples were prepared at the times indicated from uninfected (shown by the dots) and infected cells. Penton transcripts were analysed at 24 and 48 hr for all cell types. Hexon transcripts were analysed at the times shown.

MODES FOR CARRYING OUT THE INVENTION

Methods

Growth and Purification of OAV287

Figure 1:
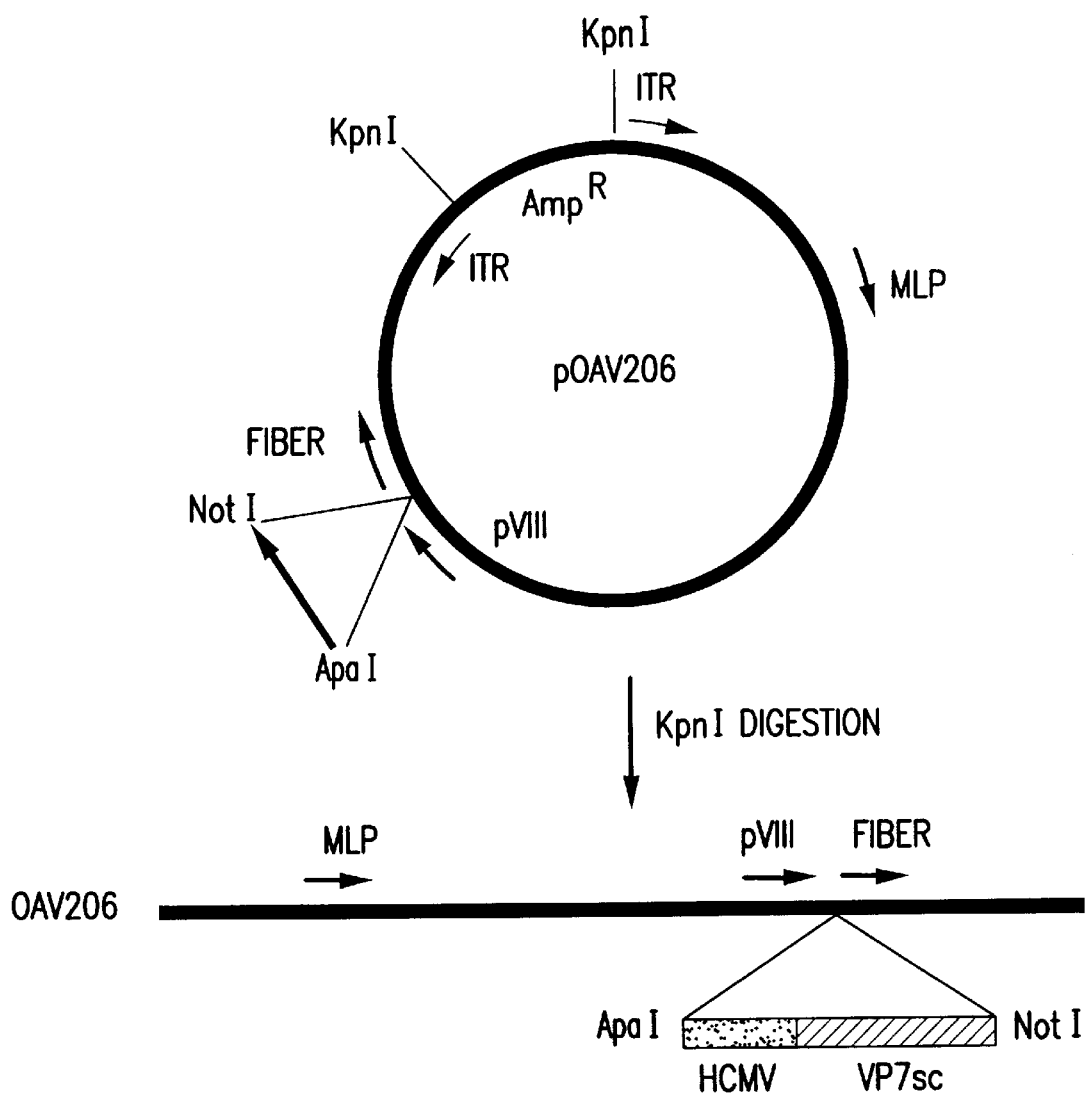
FIG. 1 shows a map of the pOAV206 plasmid and the corresponding recombinant virus which expresses the VP7sc antigen from the HCMV promoter.

The virus, isolated from sheep in 1985, was obtained from R. L. Peet, Animal Health Laboratory, Department of Agriculture, Western Australia. The virus isolate was grown in sheep foetal lung cells (line CSL503) and twice plaque-purified under solid overlay before stocks were prepared. Virus was purified from CSL503 cells as described previously (18, 22). DNA was extracted from the virus by digestion with proteinase K (23).

Cloning of Genome Fragments

Molecular techniques for manipulation, modification and transformation of plasmid DNA which were used in the work described below are described in (9) and similar publications. OAV287 DNA was digested with various restriction endonucleases including BamHI, SphI, SmaI and SalI to deduce the location of these sites (18).

The adenovirus genome has a protein covalently linked to each end of the linear dsDNA (24). The BamHI A and D fragments of approximately 8 kb and 4 kb, respectively, were identified as the terminal genomic fragments because their migration into agarose gels was dependent on the pre-digestion of viral DNA with proteinase K. The internal BamHI fragments B, C, E and F, estimated at 6.2, 5.1, 3.4 and 1.1 kb in size respectively, were separated on an agarose gel, recovered and cloned into BamHI-digested pUC13 using standard ligation and transformation procedures (9). To clone the terminal BamHI A and D fragments, viral DNA (10 μg) was digested with proteinase K (50 μg/ml in 10 mM Tris/HCl, pH8.0, containing 1 mM EDTA and 0.5% SDS) at 65° C. for 60 min to remove the terminal protein. The DNA was extracted twice with phenol/chloroform, once with ether and recovered by ethanol precipitation. The 3' ends (of unknown sequence) were then digested exo-nucleolytically with $T_4$ DNA polymerase (5 units, Toyobo, Tokyo, Japan) in the presence of dATP (100 μM) in buffer containing Tris HCL (50 mM), pH8.0, $MgCl_2$ (7 mM), 2-mercaptoethanol (7 mM) and BSA (10 μg/ml) for 15 min at 37° C. The DNA was again purified by phenol extraction and ethanol precipitation described above. To remove the single-stranded terminal regions and create blunt ends the DNA was digested with 1 unit of mung bean nuclease (Pharmacia, North Ryde, Australia) for 10 min at 37° C. in buffer contain Na acetate (30 mM), pH4.6, NaCl (50 mM) and $ZnCl_2$ (1 mM) before extraction with phenol/chloroform and recovery by ethanol precipitation. Finally the DNA was separated by electrophoresis in low-melting-point agarose. The BamHI A and D fragments were excised, recoverd by NACS column chromatography (BRL, Gaithersburg, Md. and ligated with BamHI/HincII-cut plasmid Bluescribe M13+ (Stratagene, La Jolla, Calif.) prior to transformation into E. coli JM109. Positive clones carrying fragments of the expected size were identified, restriction digested and confirmed as correct by nucleotide sequencing and comparison with partial sequence determined directly from genomic DNA. This revealed that three 3'-terminal nucleotides were removed during the cloning procedure.

Nucleotide Sequencing of the OAV287 Genome

The complete sequence of the OAV287 genome was determined by sequencing the BamHI fragments A–F using the Sanger method (25) and various kits provided by commercial suppliers. Nested deletions were constructed for the five largest fragments using a double-stranded nested deletion kit (Pharmacia). These were sequenced using standard primers. Based on newly determined sequence other nucleotide primers were synthesised using a DNA synthesizer (AB1, Model 391). In this way both strands of the entire genome and the junctions between the fragments were sequenced.

9. J. Sambrook, E. F. Fritsch, T. Maniatis, Eds., *Molecular Cloning: A Laboratory Manual* (Cold Spring Harbor Laboratory Press, Cold Spring Harbor, 1989).
18. D. B. Boyle, et al., *Vet Microbial* 41, 281–291 (1994).
22. S. H. Larsen, H. D, *Virology* 82, 182–195 (1977).
23. E. Nakano, D. Panicali, E. Paoletti, *Proc Natl Acad Sci USA* 79, 1593–1596 (1982).
24. D. M. K. Rekosh, W. C. Russell, A. J. D. Bellet, A. J. Robinson, *Cell* 11, 283–295 (1977).
25. F. Sanger, S. Nicklen, A. R. Coulson, *Proc Natl Acad Sci USA* 74, 5463–5467 (1977).

Construction of Infectious Plasmids

Techniques for the manipulation of DNA sequences and the modification of plasmids are well known in the art and described in publications such as Sambrook et al. (7). Plasmid pOAV100 was constructed by cloning a full length copy of the OAV287 genome into the KpnI site of Bluescribe M13-(Stratagene) which had been modified to remove sequences between its HindIII and SmaI sites, as previously described (the PCT Application). pOAV100 lacks the SphI site which was present in the wild-type sequence of OAV287 at position 8292. pOAV100 was further modified, using Muta-gene Phagemid (Biorad Labs, Ca) or Altered sites II (Promega, Wi) mutagenesis kits, by the incorporation of a twenty nucleotide sequence containing ApaI and NotI sites between nucleotides 22,129 and 22,130 of the genome, a location between the pVIII and fiber genes. The resulting plasmid, pOAV200, was the acceptor for gene expression cassettes which were inserted into the OAV287 genome using the ApaI/NotI sites (the PCT Application). For example, the HCMV/VP7sc promoter/gene cassette was assembled in a separate plasmid and incorporated into pOAV200 using ApaI/NotI flanking sites, forming plasmid pOAV206.

Virus OAV206/Ad5f which carried a modified fiber protein, was constructed as follows. To modify the proposed cell binding domain at the C-terminal end of the OAV fiber protein, the SphI/SalI fragment derived from bases 21.527–28.644 of the OAV287 genomic sequence was subcloned into SphI/SalI-cut plasmid pAlter-1 (Promega). Mutagenic oligo-nucleotides and the Altered sites II (Promega, Wi) mutagenesis kit were used to introduce NcoI and CelII sites at positions 23,454 and 23,894 of the sequence, respectively. Oligonucleotide primers incorporating NcoI and CelII sites were used to PCR amplify the equivalent portion of the human adenovirus type 5 genome between nucleotide positions 32,156 and 32,776 which encoded the Ad5 cell binding domain (5). This PCR fragment was digested with NcoI and CelII and cloned into the NcoI/CelII-cut recombinant pAlter-1 plasmid to replace the OAV sequences. An AgeI/SalI fragment containing the modified fiber gene was then subcloned into AgeI/SalI-cut plasmid pOAV206 to create plasmid pOAV206/Ad5f. The sequence of the modified protein created is shown in FIG. 3 (SEQ ID NOS:1 to 3

To modify the penton protein, the 13 kb XmaI/SphI fragment of OAV287 (bases 9.224–21.527) containing the penton gene was subcloned into XmaI/SphI-cut pAlter-1 and mutated by the introduction of AatII and XhoI sites at positions 12.654 and 12.674, respectively. Mutagenic oligonucleotide primers containing these restriction sites were used to PCR amplify the equivalent portion of the human Ad5 penton gene containing the helix-loop-helix RGD motif (8). Similar sequences from other adenoviruses could be used. This fragment (279bp) was subcloned into the mutated AatII/XhoI-cut pAlter-1 plasmid to replace the OAV sequences. The XmaI/SphI fragment was then subcloned into XmaI/SphI-cut pOAV206 to construct a potentially infectious plasmid, pOAV206/Ad5p. This plasmid can be used to rescue a virus (OAV206/Ad5p) carrying a modified penton protein. The derivation of the hybrid penton protein sequence is shown in FIG. 4 (SEQ ID NOS:4 and 5).

The recombinant virus, OAV211, which contained a PSA/PNPase/polyA cassette was constructed as follows. A 620bp PSA promoter fragment was isolated from white blood cell DNA by PCR amplification and subcloned into pGem-T vector (Promega Corp. Madison, Wis.). Similarly, the E. coli DeoD gene (Genbank Accession Number M60917) was amplified from genonlic DNA using PCR primers which introduced SpeI and BamHI sites at bases 105 and 849, respectively, of the Genbank sequence, and digested with those enzymes. A 513bp fragment containing an SV40 polyadenylation signal was prepared by digestion of pJC119 (9) with BamHI and SalI. This fragment was cloned in a three-way ligation with the DeoD PCR fragment into pGem/PSA vector cut with SpeI and SalI. The PSA/PNPase cassette was then excised with XbaI and SalI and subcloned into an adenovirus type 5-based plasmid pXCX3 cut with SpeI and SalI. (pXCX3 was derived from pXCX2 (10) by cloning into its XbaI site a polylinker containing KpnI SpeI EcoRV BglII SalI and sites). From there the cassette was subcloned via pGem11zf+ into the ApaI/NotI sites of pOAV200, forming pOAV211.

Rescue of Viruses

Digestion of plasmids pOAV100. pOAV200 and pOAV206/Ad5f with KpnI released the linear OAV287 or modified viral genomes. These were transfected into CSL503 cells using lipofectamine (GibcoBRL) and procedures which have been previously described (the PCT Application). Viable genomes are infectious in CSL503 cells under these conditions and virus is produced causing a cytopathic effect on the cells. pOAV206 and pOAV211, however. were rescued without KpnI digestion. This was somewhat surprising as it is generally considered that a free genomic terminus is required for rescue (11, 12). Rescued viruses were characterised by restriction enzyme digestion to confirm that their genome structures were correct. Alternatively, the DNA-Terminal protein complex of OAV was prepared by centrifugation on gradients containing 4M guanidine-HCl/2.5M CsCl at 40,000 rpm for 20–22 hr in a Ti80 rotor as described for human Ad5 (13). Rescue of large plasmids as infectious virus may be improved by co-transfecting them into CSL503 cells together with a fragment of the OAV DNA-terminal protein complex e.g. after digestion with BglI/StuI.

Infection of Cells, RT-PCR Analysis and Expression of Antigens

CSL503 ovine lung, rabbit kidney and human cell lines were mock infected or infected with viruses at a multiplicity of infection of 20 pfu/cell as described previously (14). Infection was allowed to proceed for 12–96 hr, depending on the cell line. Polyadenylated RNA was prepared from ~$10^7$ cells using standard techniques. Total cDNA was synthesised using AMV reverse transcriptase primed by oligo(dT) or a specific primer. cDNAs were amplified by PCR using primers specific to the gene of interest and analysed on agarose cells. To analyse protein expression, cells were incubated in methionine-free medium in the presence of 35S-methionine to label newly synthesised proteins. The protein of interest was recovered from cell lysates by immunoprecipitation using a specific antiserum against the expressed protein (14). Recovered proteins were analysed by SDS-polyacrylamide gel electrophoresis and detected by autoradiography or using a Phosphorimager (Molecular Dynamics).

Results

The host range of OAV287 virus is unknown but is thought to be restricted largely to ovine cells as the virus failed to grow in rabbit kidney, bovine (MDBK) and simian (CV-1) cells (1). Productive virus infection has only been observed by the present inventors in sheep ovine lung cells (CSL503 line) and to a much lesser extent in a bovine nasal turbinate cell line.

Figure 2A:
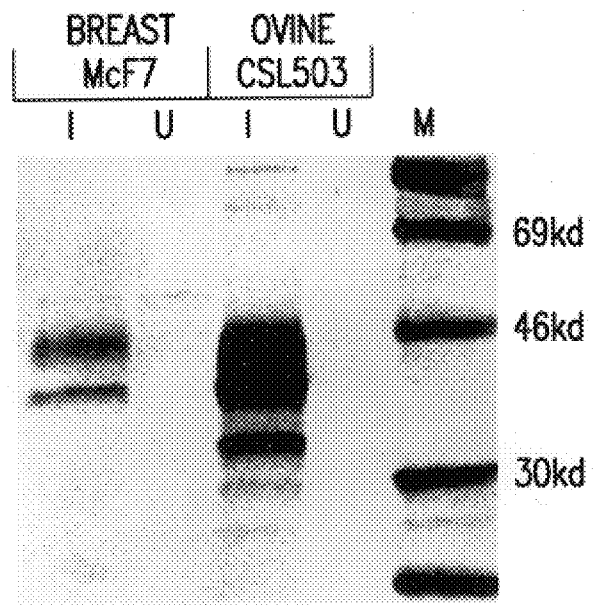
FIG. 2 (Parts A–D) investigates the expression of the VP7sc reporter protein from the HCMV promoter following infection of a variety of cell types with OAV206. (A) CSL503 ovine lung and human breast MCF7 cells (B) human prostate PC3 and LNCaP and breast T47D2 (C) human MM418E melanoma and MRC5 lung cells. (U) and (I) indicate uninfected and infected cells, respectively. (M) indicates marker proteins of the sizes indicated. In (D) CSL503, PC3 and rabbit kidney cells were infected with OAV204 which expresses VP7sc from the OAV MLP/TLS (see "the PCT applications").

As ovine adenovirus does not replicate productively in heterologous cells it is not a simple matter to determine whether the virus enters the cells but is blocked at an early stage of replication, or whether it does not enter at all. To investigate this problem and to determine the host-range of ovine adenovirus the present inventors have used the recombinant virus OAV206 which carries the human cytomegalovirus IE94 (HCMV) enhancer/promoter element functionally linked to the rotavirus VP7sc antigen gene and a polyadenylation signal (the PCT Application). The expression cassette is inserted into the ovine adenovirus genome between the genes encoding the pVIII and fiber proteins (FIG. 1). This virus was used to infect a variety of human cell types and expression of the VP7sc protein was monitored by immunoprecipitation of radiolabelled protein. It is apparent (FIG. 2A, B and C) that VP7sc expression was detected two human breast cell lines (T47D2 and McF7), one prostate cancer line (PC3) and the human lung fibroblast line MRC5. Thus, OAV206 infected these cells, despite its unique cell attachment proteins. Infection was also efficient. In McF7cells, for example, at an MOI of only 20.~30–50% of the cells expressed VP7sc as shown by immunofluorescence studies. However, not all human cell lines were infected. VP7sc expression was not detected in the human melanoma cell line MM418E or the prostate cell line LNCaP. The latter result was surprising as the prostate PC3 cell line was efficiently infected.

Cell Killing by OAV211

Figure 5A:
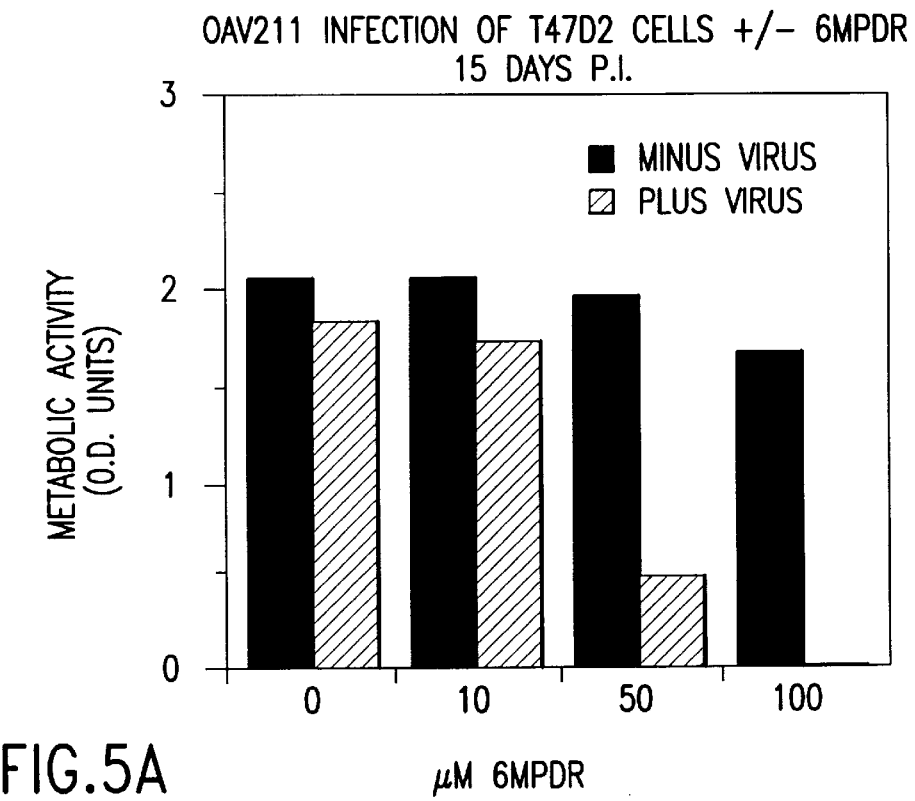
FIG. 5 (Parts A–B) shows the effect on metabolic activity of infection with OAV211 using (A) T47D2 and (B) McF7 breast cancer cells in vitro in the presence of the pro-drug 6MPDR.
Figure 5B:
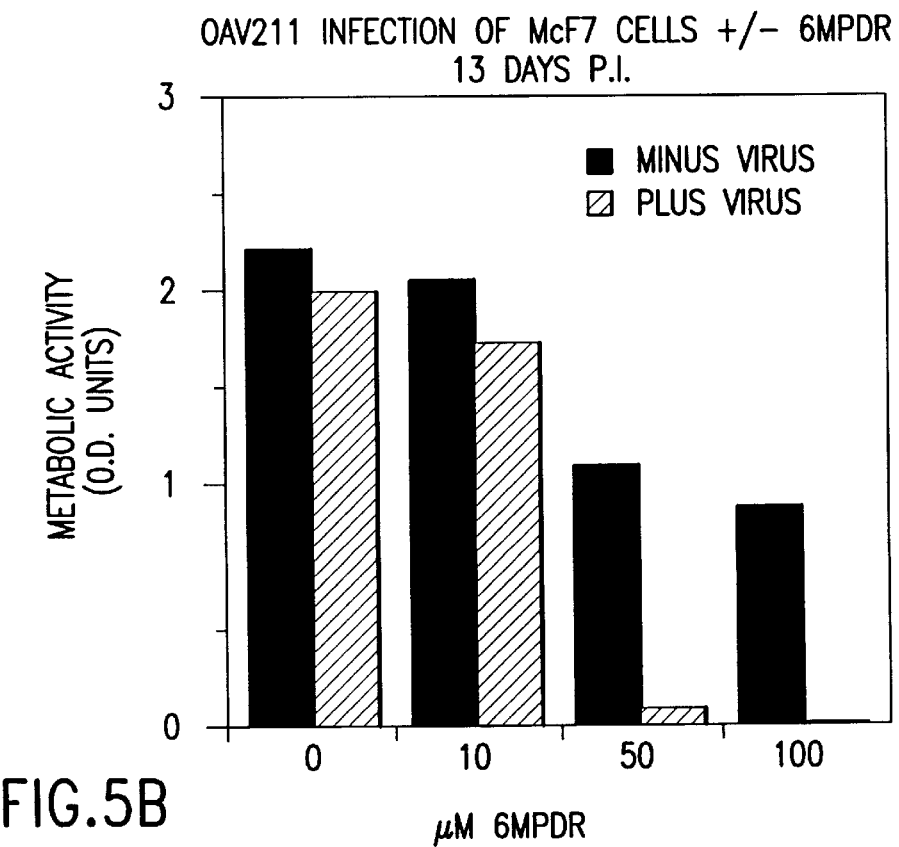

OAV211 contains the PSA/PNPase/SV40 polyA cassette. This PSA promoter fragment is not expressed in a tissue specific manner and has relatively low activity in several cell types, as shown by assays using the CAT reporter gene. PNPase is an enzyme which metabolises the pro-drug 6-methyl-purine-2'-deoxyribonucleoside (6MPDR) to the toxic product 6MP, which is toxic to cells (15). Human prostate PC3 and the breast cancer lines cells McF7 and T47D2 were infected with OAV211 at an MOI of 10. Other cells were left uninfected. Both infected and uninfected cells were incubated in the presence 0–100 $\mu$M 6MPDR for periods of up to twenty days. Metabolic activity in the cells was monitored using Alamar Blue (Alamar Biosciences Inc., Sacramento, Calif.) OAV infection had no detectable effect on PC-3. McF7 or T47D2 cells at 13 days p.i. The pro-drug (0–100 $\mu$M) had no effect on the T47D2 cells (FIG. 5A). McF7 cells showed some reduction in metabolic activity (FIG. 5B), although most of the cells recovered when the drug was removed. However, following infection with OAV211 in the presence 50–100 $\mu$M 6MPDR, both breast cancer cell lines were killed after by 13 days p.i., notwithstanding the fact that our recent work has revealed that the PSA promoter fragment has only low level activity in these cells. Similar results were obtained with the prostate PC3 cell line. The demonstration that OAV vectors can infect certain human cancer cells makes them useful for the delivery of enzyme-prodrug therapy. Considerable improvement in cell killing could be expected with a more active promoter. Other compounds such as arabinofuranosyl-2-fluoroadenine (Fludarabine) could also be used as substrates for PNPase.

Altered Cell Tropism of OAV

Figure 2B:
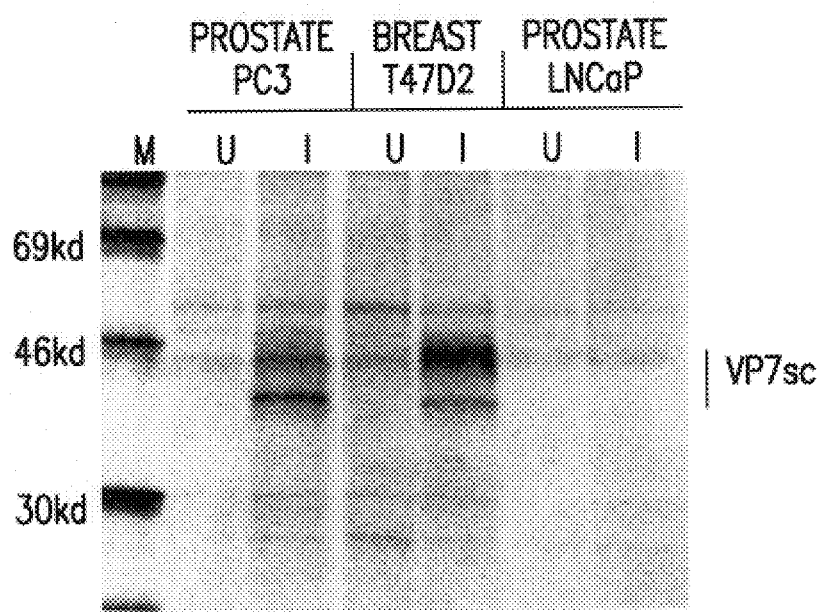
Figure 2C:
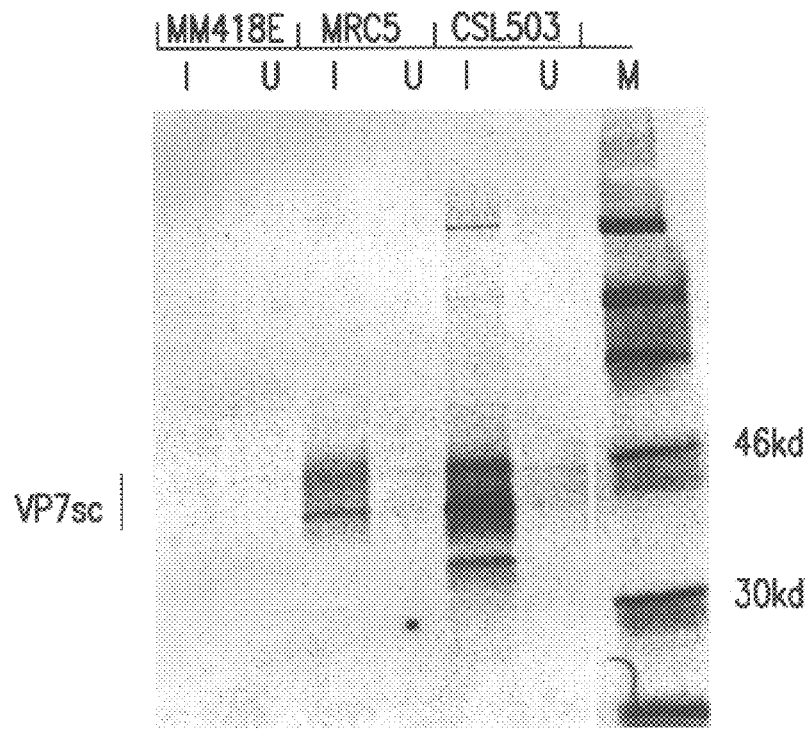
Figure 6:
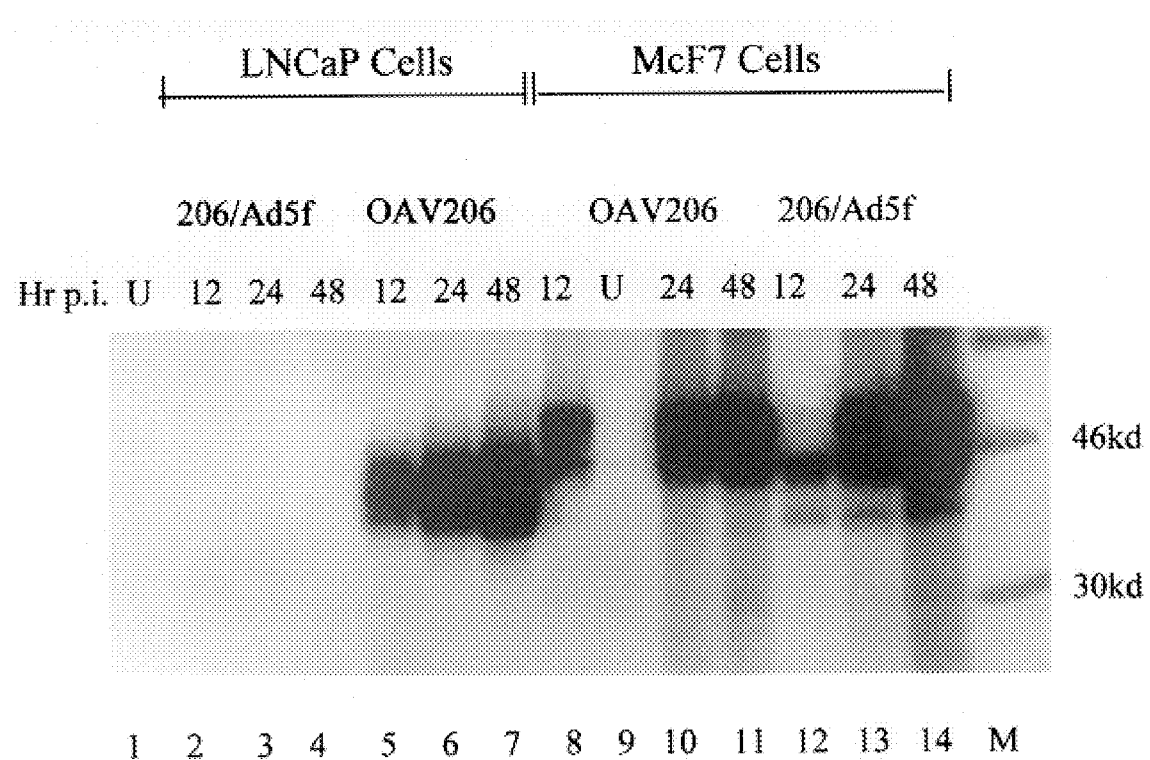
FIG. 6 investigates the expression of VP7sc in LNCaP and MCF7 cells following infection with OAV206 or OAV206Ad5f. (U) indicates uninfected cells. Times refer to hours post infection.

The cell binding domain at the tip of the fiber protein is the primary attachment site of adenoviruses with unknown receptors on the cell surface (5). By changing this domain it should be possible to alter the cell tropism of an adenovirus, provided that the integrity of the trimeric fiber protein is maintained. The cell binding domain on the fiber protein of OAV was exchanged with the equivalent region from human adenovirus type 5 as described in FIG. 3 (SEQ ID NOS: 1 to 3). The virus, OAV206/Ad5f, was rescued following transfection of the corresponding plasmid into CSL503 cells. Viruses OAV206 and OAV206/Ad5f were used to infect human LNCaP and McF7 cells. Expression of VP7sc was monitored in these cells at 12, 24 and 48 hr post infection as an indicator of whether the virus entered the cells. Mock-infected cells were monitored at 24 hr p.i. Consistent with the data in FIGS. 2A and 2B, OAV206 was able to infect in McF7. but not LNCaP cells, as shown by VP7sc expression (FIG. 6. lanes 2–4 and lanes 8, 10 and 11). However, OAV206/Ad5f infected both LNCaP and McF7 cells and expressed VP7sc efficiently (FIG. 6. lanes 5–7 and lanes 12–14). (The different size of VP7sc in these cell types reflects differences in the carbohydrate attached to the protein (14). Thus, exchanging the cell attachment domain of the OAV fiber protein with that from Ad5 allowed OAV206/Ad5f to infect human LNCaP cells which were not infected by OAV. By selecting the cell binding domains from other adenoviruses, it will be possible to change the ability of OAV to infect certain cell types. By also changing sequences in the penton protein as described in FIG. 4 (SEQ ID NOS:4 and 5), it will be possible to further define the cell tropism of OAV. The hybrid viruses would retain their abortive replication properties.

These data show clearly that ovine adenovirus can enter some, but not all, human cell types and express a foreign gene from an active promoter. It is possible to vary both the promoter and the gene in the expression cassette carried by the virus. For example, prostate tissue-specific promoters such as probasin (15) or PSMA (17), the erbB-2 promoter which is specifically active in some breast cancers (18) or the tumor-specific CEA promoter (19) could be used to achieve specific cell killing by enzyme/prodrug systems. Promoters suitably active in other tissues should be used as appropriate. Genes which could be delivered include oncogenes or tumor suppressor genes or other therapeutic genes encoding antisense or ribozyme (catalytic) RNAs, cytokines and other immune modulating proteins, vaccine antigens, proteins which catalyse processes leading to cell death and others which complement genetic defects in somatic cells. As OAV and its recombinant derivatives do not replicate productively in heterologous cells they allow the delivery and expression of genes without the risk of viral spread to non-target hosts and with minimal side effects on the host.

Analysis of OAV Promoter Function

Following infection, the OAV genome can persist in some human cells for a considerable time with little detectable effect. For example, PC3 cells were infected with OAV at an MOI of 20 and maintained in culture for periods of up to three weeks. During this time the cells showed minimal phenotypic changes in comparison with uninfected PC3 cells. At 3 weeks post infection DNA was extracted from the PC3 cells and a portion of it was amplified by PCR. The viral genome was still detectable, showing that it had persisted. In contrast, when LNCaP cells were used, the viral genome was already undetectable, at 2–5 days p.i. As LNCaP cells are not infected by OAV, this result shows that the genome must have persisted inside the PC3 cells and confirms that infection had little effect. Genome persistence and cell survival may occur due to the inactivity of OAV promoters and the consequent lack of viral protein synthesis. This would be advantageous for gene therapy, because in human adenovirus vectors, residual MLP function results in low level synthesis of highly immunogenic viral capsid proteins which stimulate an immune response. This is undesirable as it results in clearance of the virus by the cellular immune system (20). The persistence of OAV genomes in non-permissive cells should allow therapeutic gene expression to continue.

Figure 2D:
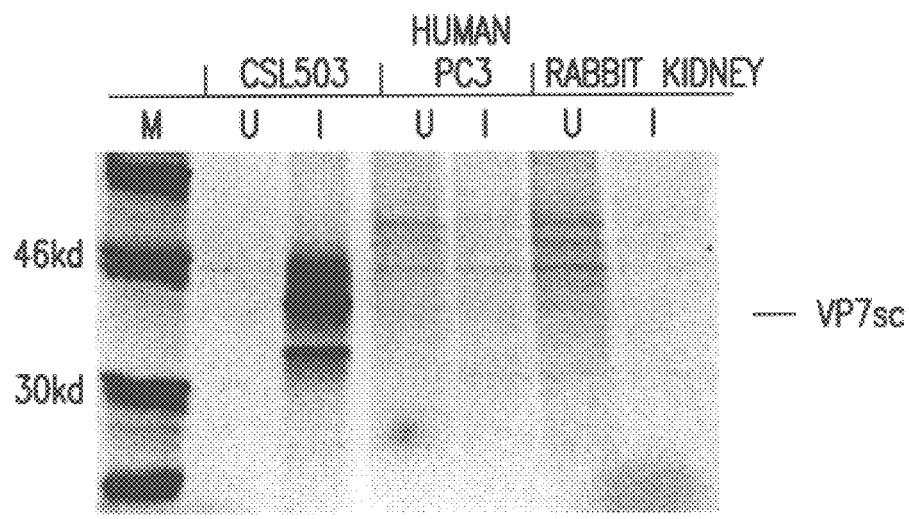

Promoter activity in OAV-infected cells was first examined indirectly by incubating cells with $^{35}$[S] methionine to radiolabel proteins. Recombinant virus (OAV204), which carries the MLP/TLS/VP7sc cassette readily expressed VP7sc in CSL503 cells (the PCT application), but did not did not express it in rabbit kidney or human prostate PC3 cells (FIG. 2D). Synthesis of late viral proteins such as hexon, fiber and penton was also undetectable by radiolabelling in these cells, although they were readily detectable in permissive CSL530.

A more sensitive study of promoter function in CSL503 and non-ovine cells was carried out using reverse transcription and PCR to look for RNA transcripts. Total polyadenylated RNA was prepared from CSL503, PC3, MRC-5, McF7, T47D2, RK15 and LNCaP cells at various times after infection with OAV206 (MOI 20 pfu/cell). cDNA was synthesised using reverse transcriptase primed by oligo(dT). Selected cDNAs were then amplified using a 5' primer from exon 2 of the TLS (the PCT application) and a 3' primer complementary to the transcript of interest. PCR products for penton and hexon (expected sizes of 606 and 740 bp, respectively) were amplified from OAV206-infected, but not uninfected CSL503 cell RNA harvested at 24 and 48 hr p.i. (FIG. 7). Products of the expected size were also amplified from fiber and IIIa transcripts. However, the hexon and penton PCR products were not detectably amplified when RNAs from any of the human or animal cell lines were analysed by RT-PCR (FIG. 7). The anticipated product was amplified for the housekeeping enzyme GAPDH in all samples. Thus, the OAV MLP does not function detectably in non-ovine cells. This is sufficient to explain why replication is abortive in these cell types.

Figure 8:
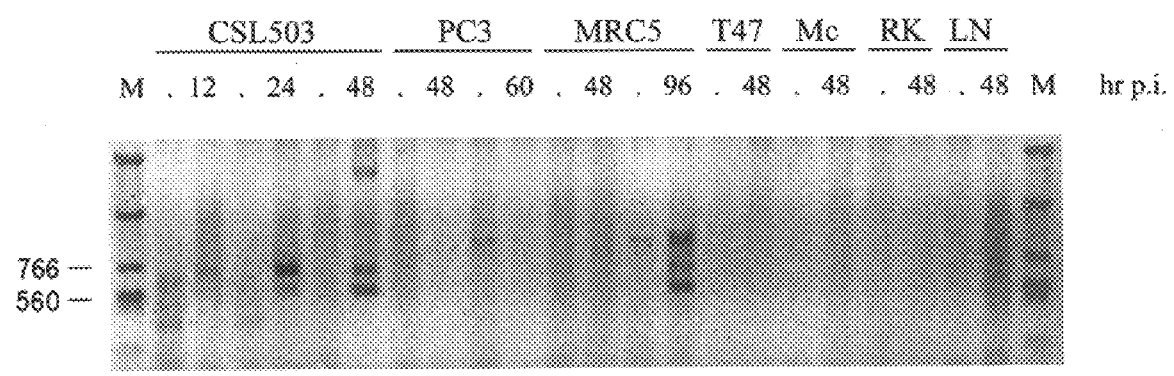
FIG. 8 shows all RT-PCR analysis of transcripts derived from a promoter located at the extreme right hand end of the OAV genome in a variety of cell types. RNA was harvested at the times shown.
Figure 6:
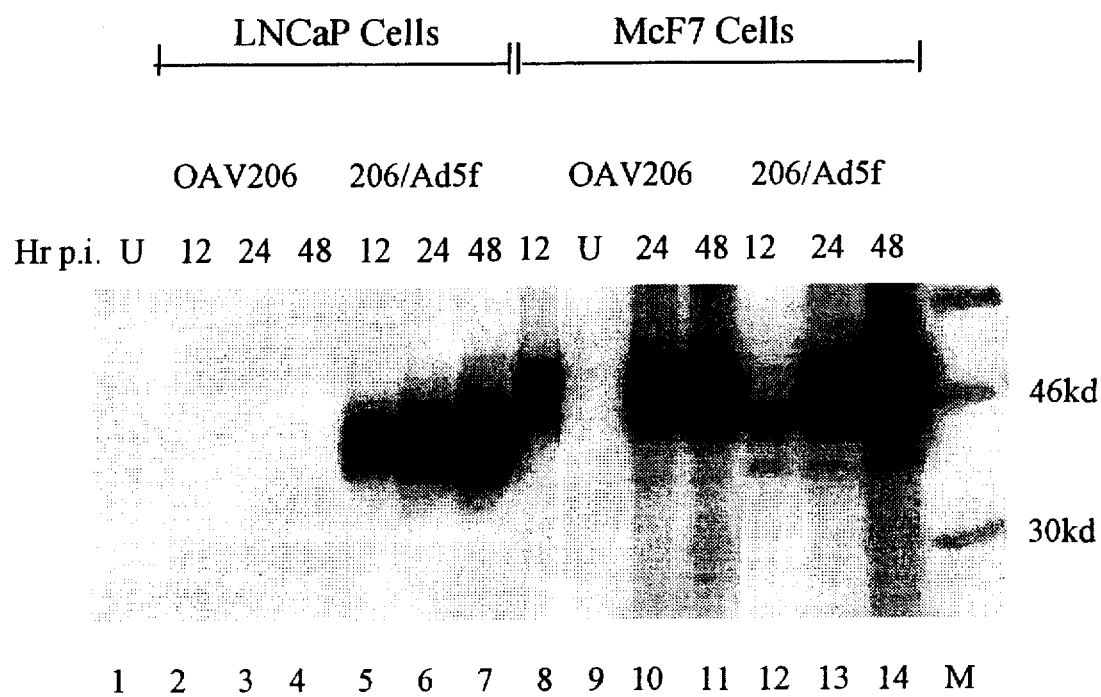

Similar observations were made for transcripts derived from an early promoter. A group of open reading frames of unknown function (tentatively named as the E3? region in the PCT application) are located at the extreme right hand end of the genome. Using RT-PCR and primers beginning at positions 26,700 and 29,220 products of ~750 and ~550 bp were amplified from polyadenylated RNAs isolated from OAV-infected, but not uninfected CSL503 cells (FIG. 8). A product of ~2,500 bp was also detected at 48 hr p.i. This was amplified from replicated genomic DNA. Nucleotide sequencing showed that the 750 and 550 bp products were produced by splicing at different locations. These RNAs are therefore transcribed in the right to left direction from an unidentified promoter which must be located between the first methionine codon on this strand (bases 29,425–29,427) and the end of the genome. The transcripts can be detected by RT-PCR as early as twelve hours p.i. and are more prominent at 24 hr p.i. (FIG. 8). Using the same primers. RT-PCR was carried out on RNA prepared from the infected and uninfected human and rabbit cells described in FIG. 7. The PCR products detected in CSL503 cells were not detected in most other OAV-infected cells (FIG. 8) showing that this early promoter does not function detectably in a variety of human and non-ovine cells. The smaller PCR products were detected in MRC5 cells at 96 hr p.i., indicating that the promoter was active at this time (FIG. 8). A product of ~900 bp derived from cellular RNA was also seen. However, the absence of the 2.5 kb product showed that DNA replication did not occur in these cells. The data show that in most non-ovine cells early and late promoter function was not detectable. OAV appears to be a benign vector in some cells while remaining capable of delivering a gene expressed from a foreign promoter.

It has been shown in the PCT Application that OAV287 recombinant vectors can infect animals and deliver foreign genes to cells of those animals. Furthermore, it has been demonstrated in the present specification that viral vectors derived from OAV287 can infect human cells and deliver therapeutic genes to those cells. From these results it will be appreciated that viral vectors derived from ovine adenoviruses and especially vectors derived from OAV287 would function as described in methods to deliver genes to humans.

In summary, OAV287 adenovirus replication in a variety of human cell lines is abortive and no detectable virus is produced. Abortive replication is accounted for by the lack of early and late promoter function. A further reduction in viral promoter activity in some cell types may be achieved by introducing a mutation in the gene for DNA Binding Protein, as shown for human adenovirus vectors (21). Ovine adenoviral vectors which abortively infect human cells and functionally express a therapeutic gene would be advantageous for use in gene therapy particularly as they would not be neutralised by antibodies to human adenoviruses. Because of their unique nucleotide sequence, OAV vectors are also unlikely to undergo homologous recombination with circulating human adenoviruses.

The method of gene therapy of the present invention using a recombinant ovine adenoviruses vector has the following advantages over the use of human or other non-human adenoviruses in gene therapy:

viral vector able to infect human cells;

viral vector is replication deficient in human cells;

low residual viral vector gene expression in human cells;

viral vector recombination with other non-ovine adenoviruses unlikely;

low probability of prior exposure to ovine adenoviruses and therefor no pre-formed antibodies to the virus vector.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

References

1. D. B. Boyle, et al., Vet Microbiol 41, 281–291 (1994).
2. S. Chiocca, et al., J Virol 70, 2939–2949 (1996).
3. S. Vrati. et al., Virology 220, 186–199 (1996).
4. J. M. White, Current Biology 3, 596–599 (1993).
5. L. J. Henry, et al., J Virol 68, 5239–5246 (1994).
6. T. J. Wickham, et al., Cell 73, 309–319 (1993).
7. J. Sambrook, et al., Eds., Molecular Cloning: A Laboratory Manual (Cold Spring Harbor Laboratory Press, Cold Spring Harbor, 1989).
8. P. Mathias, et al., J Virol 68, 6811–6814 (1994).
9. J. Sprague, et al., J. Virol. 43, 369–378 (1983).
10. R. Spessot, et al., Virology 168, 378–387 (1989).
11. K. L. Berkner, P. A. Sharp, Nuc Acids Res 11, 6003–6020 (1983).
12. D. Hanahan, Y. Gluzman, Mol Cell Biol 4, 302–309 (1984).
13. S. Miyake, et al., Proc Natl Acad Sci USA 93, 1320–1324 (1996).
14. Z. Z. Xu, et al., J gen Virol 76, 71–80 (1995).
15. E. J. Sorscher, et al., Gene Ther 1, 233–238 (1994).
16. N. M. Greenberg, et al., Mol Endocrinol 8, 230–239 (1994).
17. R. S. Israeli. et al., Cancer Res 54, 1807–1811 (1994).
18. J. D. Harris, et al., Gene Therapy 1. 170–175 (1994).
19. T. Osaki, et al., Cancer Res 54, 5258–5261 (1994).
20. Y. P. Yang, et al., Proc Natl Acad Sci USA 91, 4407–4411 (1994).
21. J. F. Engelhardt, et al., Proc Natl Acad Sci USA 91, 6196–6200 (1994).

I claim:

1. A method of delivering a nucleic acid molecule to a human cell comprising exposing the cell to a viral vector comprising:
   a DNA molecule that comprises the genome of ovine adenovirus OAV287; and
   at least one nucleic acid molecule to be expressed in the cell, such that the viral vector enters the cell and the cell expresses the nucleic acid molecule.

2. The method according to claim 1, wherein no virus replication occurs in the cell.

3. The method according to claim 1, wherein no early or late viral gene expression occurs in the cell.

4. The method according to claim 1, wherein the nucleic acid molecule is selected from the group consisting of oncogenes, tumor suppressor genes, antisense and ribozyme RNAs, genes encoding enzymes, genes encoding cytokines and other immune-modulating macromolecules, genes encoding recombinant antibodies, genes encoding lytic peptides, genes encoding vaccine antigens, genes encoding macromolecules which complement genetic defects in somatic cells, and genes encoding macromolecules which catalyze processes leading to cell death.

5. The method according claim 1, wherein the viral vector includes a cell-specific promoter operably linked to the nucleic acid molecule such that the nucleic acid molecule is expressed only in a desired target cell.

6. The method according to claim 1, wherein the viral vector is OAV211 comprising a PSA/PNPase/SV40 poly A cassette as the nucleic acid molecule to be delivered to the cell.

7. The method according to claim 1, wherein the viral vector has one or more coding regions for a coat protein of the ovine adenovirus genome, which are modified or altered.

8. The method according to claim 4, wherein the nucleic acid molecule encodes an enzyme that metabolizes a pro-drug.

9. The method according to claim 8 wherein the nucleic acid molecule encodes prokaryotic purine nucleoside phosphorylase (PNPase) and the pro-drug is 6-methyl-purine-2'-deoxyribonucleoside (6MPDR) or fludarabine.

10. The method according to claim 5, wherein the cell-specific promoter is selected from the group consisting of the rat probasin, human PSA, PSMA, erbB-2, and CEA promoters.

11. The method according to claim 10, wherein the target cell is a human prostate or breast cancer cell.

12. The method according to claim 7, wherein the coding region for the modified or altered coat protein is selected from the group consisting of fiber, hexon, and penton base proteins.

13. The method according to claim 7, wherein the modification involves the replacement of coding regions for specific ovine adenoviral proteins or parts thereof with the equivalent coding regions for proteins or parts thereof from other adenoviruses.

14. The method according to claim 7, wherein the viral vector is OAV206/Ad5f.

15. The method according to claim 7, wherein the viral vector is OAV206/Ad5p.

16. The method according to claim 7 wherein the viral vector is OAV206/Ad5f/Ad5p.

17. The method according to claim 12 such that the modification results in the vector having binding-specificity for a desired target cell.

18. A viral vector OAV211 comprising the genome of ovine adenovirus OAV287 modified to include a nucleic acid molecule comprising a PSA/PNPase/SV40 poly A cassette.

19. A viral vector OAV206/Ad5f comprising a modified genome of ovine adenovirus OAV287 such that the viral vector expresses a hybrid ovine/human adenovirus type 5 fiber protein Ad5f and not a wild type ovine adenovirus fiber protein.

20. A viral vector OAV206/Ad5p comprising a modified genome of ovine adenovirus OAV287 such that the viral vector expresses a hybrid ovine/human adenovirus type 5 penton protein Ad5p and not a wild type ovine adenovirus penton protein.

21. A viral vector OAV206/Ad5f/Ad5p comprising a modified genome of ovine adenovirus OAV287 such that the viral vector expresses hybrid ovine/human adenovirus type 5 fiber protein Ad5f and penton protein Ad5p not wild type ovine adenovirus fiber and penton proteins.

22. A method of producing a viral vector for expression of a nucleic acid molecule in a human cell, the method comprising:
    constructing a plasmid by cloning a full length copy of the genome of ovine adenovirus OAV287 into a plasmid;
    adding to the plasmid an expression cassette comprising a nucleic acid molecule to be expressed in the human cell;
    transfecting a producer cell with the plasmid such that the viral vector is produced by the cell; and recovering the viral vector.

23. A method of delivering a recombinant nucleic acid molecule to a human cell, the method comprising contacting the cell with a biologically active, naturally assembled capsid of ovine adenovirus OAV287 containing the recombinant nucleic acid molecule, such that the capsid enters the cell and the cell expresses the recombinant nucleic acid molecule.

24. The method according to claim 23, wherein no virus replication occurs in the cell.

25. The method according to claim 23, wherein no early or late viral gene expression occurs in the cell.

26. The method according to claim 23, wherein the recombinant nucleic acid molecule comprises nucleotide sequences selected from the group consisting of genes coding for oncogenes, tumor suppressor genes, antisense and ribozyme RNAs, genes encoding enzymes, genes encoding cytokines and other immune modulating macromolecules, genes encoding recombinant antibodies, genes encoding lytic peptides, genes encoding vaccine antigens, genes encoding macromolecules which complement genetic defects in somatic cells, and genes encoding macromolecules which catalyze processes leading to cell death.

27. The method according claim 23, wherein the recombinant nucleic acid molecule includes a nucleotide sequence encoding a cell-specific promoter operably linked to a coding nucleotide sequence such that the coding nucleotide sequence is expressed only in a desired target cell.

28. The method according to claim 23, wherein the ovine adenoviral capsid has one or more coat proteins modified or altered.

29. The method according to claim 26, wherein the recombinant nucleic acid molecule comprises a nucleotide sequence encoding an enzyme which metabolizes a pro-drug.

30. The method according to claim 29, wherein the enzyme is prokaryotic purine nucleoside phosphorylase (PNPase) and the pro-drug is 6-methyl-purine-2'-deoxyribonucleoside (6MPDR) or fludarabine.

31. The method according to claim 27, wherein the cell-specific promoter is selected from the group consisting of the rat probasin, human PSA, PSMA, erbB-2, and CEA.

32. The method according to claim 31, wherein the target cell is a human prostate or breast cancer cell.

33. The method according to claim 31, wherein the recombinant nucleic acid molecule comprises nucleotide sequences coding for the PSA promoter linked to the PNP gene.

34. The method according to claim 28, wherein the modified or altered coat protein is selected from the group consisting of fiber, hexon, and penton base proteins.

35. The method according to claim 28, wherein the modification involves the replacement of specific ovine adenoviral coat proteins or parts thereof with the equivalent coat proteins or parts thereof from adenoviruses.

36. The method according to claim 34, such that the modification or alteration results in the capsid having binding-specificity for a desired target cell.

37. The method according to claim 34, wherein the capsid contains a hybrid ovine/human adenovirus type 5 fiber protein Ad5f and not a wild type ovine adenovirus fiber protein.

38. The method according to claim 34, wherein the capsid contains a hybrid ovine/human adenovirus type 5 penton protein Ad5p and not a wild type ovine adenovirus penton protein.

39. The method according to claim 34, wherein the capsid carries hybrid ovine/human adenovirus type 5 fiber protein Ad5f and penton protein Ad5p and not wild type ovine adenovirus fiber and penton proteins.

40. A biologically active, naturally assembled viral particle comprising a capsid of ovine adenovirus OAV287 and a recombinant nucleic acid molecule to be delivered to a human cell.

41. The viral particle according to claim 40, wherein the recombinant nucleic acid molecule comprises nucleotide sequences selected from the group consisting of genes coding for oncogenes, tumor suppressor genes, antisense and ribozyme RNAs, genes encoding enzymes, genes encoding cytokines and other immune modulating macromolecules, genes encoding recombinant antibodies, genes encoding lytic peptides, genes encoding vaccine antigens, genes encoding macromolecules which complement genetic defects in somatic cells, and genes encoding macromolecules which catalyze processes leading to cell death.

42. The viral particle according to claim 40, wherein the recombinant nucleic acid molecule comprises a nucleotide sequence encoding an enzyme which metabolizes a pro-drug.

43. The viral particle according to claim 40, wherein the recombinant nucleic acid molecule comprises a nucleotide sequence encoding a cell-specific promoter operably linked to a coding nucleotide sequence such that the coding nucleotide sequence is expressed only in a desired target cell.

44. The viral particle according to claim 40, wherein the recombinant nucleic acid molecule comprises a nucleotide sequence encoding a PSA/PNPase/SV40 poly A cassette.

45. The viral particle according to claim 42, wherein the enzyme is prokaryotic purine nucleoside phosphorylase (PNPase) and the pro-drug is 6-methyl-purine-2'-deoxyribonucleoside (6MPDR) or fludarabine.

46. The viral particle according to claim 43, wherein the target cell is a human prostate or breast cancer cell.

47. The viral particle according to claim 43, wherein the cell-specific promoter is selected from the group consisting of the rat probasin, human PSA, PSMA, erbB-2, and CEA.

48. The viral particle according to claim 46, wherein the recombinant nucleic acid molecule comprises nucleotide sequences coding for the PSA promoter linked to the PNP gene.

49. A biologically active, naturally assembled viral particle comprising a capsid of ovine adenovirus OAV287 and a recombinant nucleic acid molecule to be delivered to a human cell, wherein the capsid contains a hybrid ovine/human adenovirus type 5 fiber protein Ad5f and not wild-type ovine adenovirus fiber protein.

50. A biologically active, naturally assembled viral particle comprising a capsid of ovine adenovirus OAV287 and a recombinant nucleic acid molecule to be delivered to a human cell, wherein the capsid contains a hybrid ovine/human adenovirus type 5 penton protein Ad5p and not wild-type ovine adenovirus penton protein.

51. A biologically active, naturally assembled viral particle comprising a capsid of ovine adenovirus OAV287 and a recombinant nucleic acid molecule to be delivered to a human cell, wherein the viral particle contains a hybrid ovine/human adenovirus type 5 fiber protein Ad5f and penton protein Ad5p and not wild-type ovine adenovirus fiber and penton proteins.

* * * * *

UNITED STATES PATENT AND TRADEMARK OFFICE
CERTIFICATE OF CORRECTION

PATENT NO. : 6,020,172
DATED : February 1, 2000
INVENTOR(S) : Gerald Wayne Both

It is certified that error appears in the above-identified patent and that said Letters Patent is hereby corrected as shown below:

<u>Drawings,</u>
The drawing sheet, consisting of Fig. 6, should be deleted to be replaced with the drawing sheet, consisting of Fig. 6, as shown on the attached page.

Signed and Sealed this

Thirtieth Day of April, 2002

*Attest:*

JAMES E. ROGAN
*Director of the United States Patent and Trademark Office*

*Attesting Officer*

SEQUENCE LISTING

<160> NUMBER OF SEQ ID NOS: 5

<210> SEQ ID NO 1
<211> LENGTH: 16
<212> TYPE: PRT
<213> ORGANISM: Ovine adenovirus

<400> SEQUENCE: 1

Asn Ala Leu Met Val Pro Lys Leu Gly Thr Gly Leu Ser Phe Asp Ser
 1               5                  10                  15

<210> SEQ ID NO 2
<211> LENGTH: 14
<212> TYPE: PRT

```
<213> ORGANISM: Ovine adenovirus

<400> SEQUENCE: 2

Thr Gly Ala Ile Thr Val Gly Asn Lys Asn Asn Asp Lys Leu
  1               5                  10

<210> SEQ ID NO 3
<211> LENGTH: 182
<212> TYPE: PRT
<213> ORGANISM: Ovine adenovirus

<400> SEQUENCE: 3

Thr Leu Trp Thr Thr Pro Ala Pro Ser Pro Asn Cys Arg Leu Asn Ala
  1               5                  10                  15

Glu Lys Asp Ala Lys Leu Thr Leu Val Leu Thr Lys Cys Gly Ser Gln
                 20                  25                  30

Ile Leu Ala Thr Val Ser Val Leu Ala Val Lys Gly Ser Leu Ala Pro
             35                  40                  45

Ile Ser Gly Thr Val Gln Ser Ala His Leu Ile Ile Arg Phe Asp Glu
         50                  55                  60

Asn Gly Val Leu Leu Asn Asn Ser Phe Leu Asp Pro Glu Tyr Trp Asn
 65                  70                  75                  80

Phe Arg Asn Gly Asp Leu Thr Glu Gly Thr Ala Tyr Thr Asn Ala Val
                 85                  90                  95

Gly Phe Met Pro Asn Leu Ser Ala Tyr Pro Lys Ser His Gly Lys Thr
            100                 105                 110

Ala Lys Ser Asn Ile Val Ser Gln Val Tyr Leu Asn Gly Asp Lys Thr
        115                 120                 125

Lys Pro Val Thr Leu Thr Ile Thr Leu Asn Gly Thr Gln Glu Thr Gly
    130                 135                 140

Asp Thr Thr Pro Ser Ala Tyr Ser Met Ser Phe Ser Trp Asp Trp Ser
145                 150                 155                 160

Gly His Asn Tyr Ile Asn Glu Ile Phe Ala Thr Ser Ser Tyr Thr Phe
                165                 170                 175

Ser Tyr Ile Ala Gln Gln
            180

<210> SEQ ID NO 4
<211> LENGTH: 20
<212> TYPE: PRT
<213> ORGANISM: Ovine adenovirus

<400> SEQUENCE: 4

Leu Thr Lys Gly Asn Ile Ser Pro Leu Leu Asp Val Asp Ala Tyr Gln
  1               5                  10                  15
Ala Ser Leu Lys
             20

<210> SEQ ID NO 5
<211> LENGTH: 25
<212> TYPE: PRT
<213> ORGANISM: Ovine adenovirus

<400> SEQUENCE: 5

Lys Pro Gln Lys Lys Pro Val Leu Glu Pro Val Met Gln Asp Glu Asn
  1               5                  10                  15
Gly Val Ser Tyr Asn Glu Lys Ile Ser
             20                  25
```